United States Patent
Hepp et al.

(10) Patent No.: US 11,351,052 B2
(45) Date of Patent: Jun. 7, 2022

(54) METHOD FOR PRODUCING A HAND ORTHOSIS AND HAND ORTHOSIS

(71) Applicant: HKK BIONICS GMBH, Ulm (DE)

(72) Inventors: Dominik Hepp, Jettingen-Scheppach (DE); Tobias Knobloch, Ulm (DE)

(73) Assignee: HKK BIONICS GMBH, Ulm (DE)

( * ) Notice: Subject to any disclaimer, the term of this patent is extended or adjusted under 35 U.S.C. 154(b) by 0 days.

(21) Appl. No.: 17/479,687

(22) Filed: Sep. 20, 2021

(65) Prior Publication Data

US 2022/0000649 A1 Jan. 6, 2022

Related U.S. Application Data

(63) Continuation of application No. PCT/EP2020/057632, filed on Mar. 19, 2020.

(30) Foreign Application Priority Data

Mar. 19, 2019 (EP) .................................... 19163907

(51) Int. Cl.
*A61F 5/01* (2006.01)
*B33Y 50/00* (2015.01)
(Continued)

(52) U.S. Cl.
CPC .............. *A61F 5/013* (2013.01); *A61B 5/107* (2013.01); *A61F 5/30* (2013.01); *B33Y 50/00* (2014.12); *B33Y 80/00* (2014.12)

(58) Field of Classification Search
CPC .......... A61F 5/013; A61F 5/30; A61F 5/0118; A61F 5/05875; A61F 5/10; A61F 5/05866; A61F 2005/0137; A61F 2007/0037; A61F 13/105; A61F 5/01; A61F 2007/0098; A61F 13/104; A61F 2007/0038; A61F 2/586; A61F 2005/0186; A61F 2/72; A61F 7/007; A61F 5/3723; A61F 5/05858;
(Continued)

(56) References Cited

U.S. PATENT DOCUMENTS 5,178,137 A 1/1993 Goor et al.
2015/0359653 A1 12/2015 Diez et al.
(Continued)

FOREIGN PATENT DOCUMENTS

CN 105997319 A 10/2016
DE 10 2013 001 732 A1 8/2014
(Continued)

*Primary Examiner* — Ophelia A Hawthorne
(74) *Attorney, Agent, or Firm* — Muncy, Geissler, Olds & Lowe, P.C.

(57) ABSTRACT

A method for producing a hand orthosis, including the steps of: Producing an impression of at least one finger of a patient's hand and at least a part of a forearm, producing a finger section from a reproduction based on the impression, incorporating at least one finger segment in the finger section side corresponding to the hand surface, detecting the physiology of the patient's forearm using at least one captured image from the reproduction together with the finger section, thereby producing a digital 3D model, generating a rail based on the produced digital 3D model, securing at least one force-introducer onto or into the rail, securing a proximal end of the at least one finger segment to a distal end of the rail, and coupling the at least one force-introducer to the at least one finger segment. A hand orthosis is also provided.

14 Claims, 8 Drawing Sheets

(51) Int. Cl.
*B33Y 80/00* (2015.01)
*A61B 5/107* (2006.01)
*A61F 5/30* (2006.01)

(58) Field of Classification Search
CPC ...... A61F 5/05841; A61F 5/0102; A61F 5/34; A61F 7/02; A61F 7/00; B33Y 50/00; B33Y 80/00; A41D 19/01547; A41D 19/0024; A41D 19/0017; A41D 19/00; A41D 19/0058; A41D 19/0062; A41D 13/081; A41D 19/01; A41D 19/04; A41D 19/0006; A41D 19/0037; A41D 13/08; A41D 13/088; A41D 31/245; A41D 27/10; A41D 13/087; A41D 2400/32; A41D 2600/10; A41D 27/12; A41D 13/084; A41D 2400/10; A41D 19/01535; A41D 19/01541

See application file for complete search history.

(56) References Cited

U.S. PATENT DOCUMENTS

| | | |
|---|---|---|
| 2017/0266075 A1 | 9/2017 | Becchi et al. |
| 2020/0281798 A1 | 9/2020 | Hepp et al. |

FOREIGN PATENT DOCUMENTS

| | | |
|---|---|---|
| EP | 3 263 086 A1 | 1/2018 |
| EP | 3 459 505 A1 | 3/2019 |

METHOD FOR PRODUCING A HAND ORTHOSIS AND HAND ORTHOSIS

This nonprovisional application is a continuation of International Application No. PCT/EP2020/057632, which was filed on Mar. 19, 2020, and which claims priority to European Patent Application No. 19163907.9, which was filed on Mar. 19, 2019, and which are both herein incorporated by reference.

BACKGROUND OF THE INVENTION

Field of the Invention

The present invention relates to a method for producing a hand orthosis. The invention further relates to a hand orthosis for flexing and/or stretching at least one finger of a patient's hand, comprising a finger section for receiving at least one finger of a patient's hand, of preferably the entire patient's hand, and a rail for at least partially grasping a patient's forearm, as well as a force-introducer secured to the rail which is coupled to at least one finger segment corresponding to the finger of the patient's hand, wherein the at least one finger segment has a starting segment coupled to the rail and an end segment coupled to the force-introducer.

Description of the Background Art

In the production process described in EP 3 459 505 A1 (which corresponds to U.S. 2020/0281798, which is incorporated herein by reference, a glove section is created by applying silicone to an impression taken from a patient's hand. The physiology of the patient's forearm is captured using a scan of the patient's hand wearing the glove section, and a model is created. Based on this, a rail is created using a generative production process. EP 3 459 505 A1 also describes a hand orthosis. This orthosis has proven itself well.

A disadvantage of the conventional art, however, is that the patient must be physically present during most steps of the production process, which makes the production of the hand orthosis more complex

SUMMARY OF THE INVENTION

It is therefore an object of the present invention to provide a method for producing a hand orthosis that is as easy as possible to carry out, and to provide a hand orthosis that also allows for the finger segments to be bent and stretched as naturally as possible.

In an exemplary embodiment, a method for producing a hand orthosis is provided that includes a finger section for receiving a patient's hand, a rail for at least partially grasping a patient's forearm, and at least one finger segment coupled to a force-introducer for flexing and/or stretching at least one finger of a patient's hand, has in particular the following steps: Producing an impression of at least one finger of a patient's hand and of at least one part of a patient's forearm, preferably producing an impression of all fingers or of the entire patient's hand and preferably of the entire patient's forearm; Producing a finger section using the impression or using a reproduction based on the impression of the at least one finger of the patient's hand, preferably of all fingers of the patient's hand; Incorporating at least one finger segment into the finger section side corresponding to the hand surface; Detecting the physiology of the patient's forearm using at least one captured image, preferably a 3D scan, of the impression or of a reproduction of the forearm based on the impression together with the finger section and generating a digital 3D model on the basis of the at least one captured image, preferably on the basis of the 3D scan; Generating a rail on the basis of the generated digital 3D model; Securing at least one force-introducer onto or into the rail; Securing the proximal end of the at least one finger segment to the distal end of the rail; and Coupling the at least one force-introducer to the at least one finger segment, preferably in the region of the distal end.

Detecting the physiology of the patient's forearm using the at least one captured image, in particular using the 3D scan of the impression or the reproduction of the forearm based on the impression together with the finger section, makes it possible to produce the hand orthosis largely independently of the patient.

The finger section may be a component of a glove section. The finger section may further be formed from a single finger stall or a plurality of finger stalls for receiving individual fingers of a patient's hand. Advantageously, it is possible for the finger stalls to be combined to make a monolithically formed finger section or a glove section monolithically formed from the finger section. There is further the possibility that two or more of the finger stalls are joined to form a common finger section, while at least one other finger stall is separate from the joined finger stalls.

The impression preferably forms a negative of the finger and/or the patient's hand and/or the forearm, from which a reproduction to be regarded as positive is then generated, which can be used for the further method steps for producing the hand orthosis.

Alternatively, the impression can be used as a positive which is immediately available for the further method steps. The creation of a reproduction or a physical model can be dispensed with in this case.

The impression is preferably produced in several parts, in particular by two shells. After solidification, the at least two shells of the impression can be connected to each other on the inside to form a closed part. Alternatively, separate impressions can be created of the patient's hand and forearm, which are then joined together. In this context, it is particularly advantageous if the impression is a plaster cast. It is also preferred if the reproduction based on the impression of the at least one finger of the patient's hand and/or forearm is made of plaster.

The captured image can be a 3D scan but also any other 3D imaging method. As an alternative to a 3D scan, the captured image can also be taken by a camera—preferably a 3D camera or even a stereo camera—and a digital 3D model can be generated or calculated on the basis of this captured image. In a further alternative embodiment, one or more cameras can also create a captured image of the impression or of the reproduction of the forearm based on the impression together with the glove section from different angles. A 3D model can then be created or calculated using triangulation, for example. Alternatively, the creation of a digital 3D model is also possible by means of structured illumination, with the help of a time of flight camera (TOF) or by means of interferometry.

It is particularly advantageous if the impression is created with the patient's hand in a flexed position. A flexed position is understood to mean in particular a gripping position. This is achieved by means of extension of the wrist by 10 degrees to 30 degrees, preferably 15 degrees to 20 degrees and/or by means of extension (maximum 10 percent flexion) of the MCP joint (metacarpophalangeal joint) and/or by means of flexion of the PIP joint (proximal interphalangeal joint)

and/or the DIP joint (distal interphalangeal joint) by 20 degrees to 50 degrees and/or by the thumb being in an opposition position or in a lateral position. In particular, it is preferred that all fingers are in a slight spread position relative to each other, i.e., there should be a space or gap of at least 5 mm between the index, middle, and ring fingers at the level of the PIP. The ring finger and the little finger can be closer together, i.e., have a distance of less than 5 mm to the adjacent finger.

In this context, it is particularly provided that the bent position is held by means of a positioning device. This ensures the optimum posture of the hand or fingers and facilitates the creation of the impression. A suitable positioning device would be a block or a wedge or various wedges that can be combined with each other. In an alternative embodiment, the holding device can also be a spherical or partially spherical structure, for example a ball, which is gripped by the patient's hand.

If the positioning device used is formed as a part-spherical structure, the curved surface can be used to image the curved joints of the patient's finger, whereas the uncurved planar surface of the part-spherical structure can be used to image the stretched joints of the patient.

Advantageously, the glove section can be created by applying silicone to the impression. The silicone can be applied by applying several layers of silicone. In an alternative embodiment, molds adapted to the impression can be created by means of a generative process, and the molds can subsequently be filled with silicone. The silicone formed in this way can then be applied to the impression. Alternatively, the silicone can also be produced and molded using a 3D printing process, which provides a higher degree of automation for producing the hand orthosis.

Furthermore, it is advantageous if different silicones with different degrees of hardness are used to create the finger section, preferably the glove section. This makes it possible to produce parts of the finger section, in particular of a glove section which are subject to bending or stretching or which come into contact with the hand, with a first silicone, and parts of the finger section, in particular of the glove section which are subject to high stresses, with a second silicone, wherein the first silicone has a lower degree of hardness than the second silicone. In particular in the area where the at least one finger segment is incorporated, it is therefore preferable to use silicone with a softer degree of hardness (for example Shore A 15 to 25). On the other hand, for stiffening PIP and/or DIP joints and/or for producing stable pull rings at entry openings for the finger segments, it is advantageous to use a silicone with a harder degree of hardness in the range of Shore A 50 to Shore A 70, preferably Shore A 60. To increase stability, it is also possible to incorporate or embed other, in particular inert, stiffening agents into the softer silicone instead of a silicone with a higher degree of hardness. Pins made of ceramic and metal, or wire gauze can be considered here.

For stabilizing and/or stiffening the PIP joint and/or the DIP joint, it may also be advantageous to additionally incorporate in the silicone a material which has a higher degree of hardness than the silicone.

Furthermore, it is preferred if the at least one finger segment is incorporated in the silicone by means of a silicone punch. This allows for an exact, predefined amount of silicone to be provided and used.

Furthermore, it is provided that the silicone finger section or the silicone glove comprising a plurality of finger sections is crosslinked by the action of heat, for example in an oven.

In particular, it is preferred if the length of the at least one finger segment is adapted to the length of a patient's finger by arranging and coupling one or more module segments between a starting segment coupled to the rail and an end segment connected to the force-introducer. By coupling a different number of module segments between the starting segment and the end segment, it is possible to produce finger segments of different lengths.

It is particularly advantageous if the module segment is formed as a linear segment or as an articulated segment and if the length of the at least one finger segment of the finger section or of the glove section is adapted by combining one or more articulated segments with one or more linear segments. The articulated segments thereby enable a tilting movement while the linear segments enable a translational movement and, in particular, an elongation of, and a compensation for, the change in length of the skin on an outer side of the finger. Each finger segment thus includes a starting segment, an end segment and at least one articulated segment as well as at least one linear segment.

For the use of the hand orthosis in people with particularly small fingers, especially with small thumbs, it is also possible that only one articulated segment is incorporated between the starting segment and the end segment, or a coupled plurality of articulated segments.

In one embodiment, the physiology of the forearm and thereby the digital 3D model can be detected using the at least one captured image, in particular using the 3D scan of the impression or the impression-based reproduction of the forearm together with the finger section or the glove section, and with padding applied to at least parts of the finger section or the glove section and/or at least to parts of the impression or the one reproduction based on the at least one impression. In particular, the padding is applied at least to the portions of the finger section or the glove section that come into contact with the hand. Consequently, in this embodiment, the silicone is first applied to the finger section or glove section and then the padding is applied to the silicone. Finally, the 3D model is created using the at least one captured image, preferably using the 3D scan. The captured image may also be created by one or more cameras, and the 3D model may be created or calculated based on one or more scans. In this case, the camera may be a 2D camera or a 3D camera or a stereo camera. It is also possible to create or calculate the digital 3D model using structural illumination or time of flight measurements or triangulation.

Alternatively, for a 3D model created without padding, an offset can be added to this model for the application of padding. The offset can correspond to the height of the padding applied later or, in an alternative embodiment, be selected to be less than the height of the padding. As a result, when the padding is applied to the finger section or the glove section and to the rail, the play between the hand orthosis and the hand is reduced, so that the hand orthosis fits the hand more tightly and securely.

In another alternative embodiment, it is possible that the offset calculates, i.e., extracts, the subsequent padding, and thus a cut of the padding can subsequently be automatically produced by an automated process; its shaping is based on the 3D model having the offset.

Preferably, the padding to be applied can also be a padding produced directly generatively, in particular by means of 3D printing, the shaping of which is based on the 3D model having the offset.

It is also possible that, based on the 3D model, a template for padding to be cut to size, in particular manually, is first created and/or output, and that the padding is then cut to size based on the created template and is provided before it is applied to the finger section or the glove section and/or the rail. Preferably, the template is formed from paper or from cardboard and thus utilizes renewable raw materials.

The padding is applied to at least a portion of a dorsum of the finger section or glove section and/or at least a portion of the rail. In a preferred embodiment, the entire finger section or the entire glove section and the entire rail are padded. This increases comfort when wearing the hand orthosis.

It has also proven useful if, prior to detecting the physiology of the forearm using the at least one captured image, at least one marking line or a plurality of marking points is applied to the impression or to the reproduction based on the impression to define a later contour or the edge course of the rail. It contributes to the accurate fit of the later hand orthosis if, in addition, the padding is applied prior to detection.

To improve the fit of the hand orthosis on the hand or forearm, at least one palm support and/or at least one forearm support can be added to the digital 3D model. The palm support and/or forearm support can then preferably be produced together with the rail based on the created 3D model. A plurality of palm supports and/or forearm supports molded onto the rail is also useful for a particularly secure fit of the hand orthosis on the patient's limbs.

It is particularly advantageous if the rail and/or the palm support and/or the forearm support are produced by means of a generative production process. This can be done in particular by a 3D printing process. Suitable generative production processes are laser sintering, laser or screen printing, laser beam melting, electron beam melting, fused layer modeling, multi-jet modeling, poly-jet modeling, layer laminated manufacturing, digital light processing.

The force-introducer are preferably embodied as servomotors, in particular individually controllable servomotors. The force-introducer assigned to the finger segment in question is connected to a first end of a coupling element, in particular to the first end of a wire, preferably a nitinol wire, the other end of which is connected to the end segment. The force-introducer are secured in recesses of the rail.

In order to provide a smooth surface of the hand orthosis, it is therefore advantageous in a further, in particular final, method step if a cover, preferably a covering hood or cover, is applied to the surface of the rail facing away from the forearm and preferably screwed to the rail. This then covers the often sensitive force-introducer or servomotors.

The object underlying the hand orthosis is achieved by the features of claim 15, in particular in that at least one articulated segment for a tilting connection with the adjacent segment, and preferably also at least one linear segment with limited axial movability, are arranged between the starting segment and the end segment. Each of the finger segments thus consists of a starting segment, an end segment and at least one intermediary articulated segment, and preferably additionally of at least one linear segment located between the starting segment and the end segment. The articulated segments enable a bending or tilting movement or a pivoting movement of the finger segments, wherein the pivoting movement enables at least an angle of 10 degrees to 20 degrees—preferably 18 degrees. The linear segments provide for a translational movement, thus also in particular for an elongation of, and compensation for, the change in length of the skin on the outside of the finger. This allows for the length or the distance between individual articulated segments to be increased in order to adapt the length of the finger segments to the length of the patient's fingers.

Advantageously, the segments have at least one bayonet slot on a first end face and at least one bayonet hook corresponding to the bayonet slot on a second end face for forming a bayonet joint-producing bayonet connection between adjacent segments.

In particular, it is provided that the linear segments and the articulated segments have several, preferably four, bayonet hooks evenly distributed over the circumference and several, preferably four, corresponding bayonet slots. In this case, the upper bayonet hooks of the articulated segments facing away from the finger section have little to no play in the corresponding bayonet slots, while the upper bayonet slots of the linear segments facing away from the finger section and the lower bayonet slots of the linear segments facing towards the finger section have play, preferably the same play, and thus provide a translation, i.e., a straight-line displacement of the bayonet hooks in the bayonet slots.

In order to enable a tilting movement, the upper bayonet slots of the articulated segment facing away from the finger section also each have a projection, which is formed with an angled projection surface. The upper bayonet hooks facing away from the finger section and the lower bayonet hooks facing towards the finger section also preferably have the same small play in the articulated segments, as a result of which a tilting movement of the articulated segments is made possible, yet a translational movement is at least almost completely prevented.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
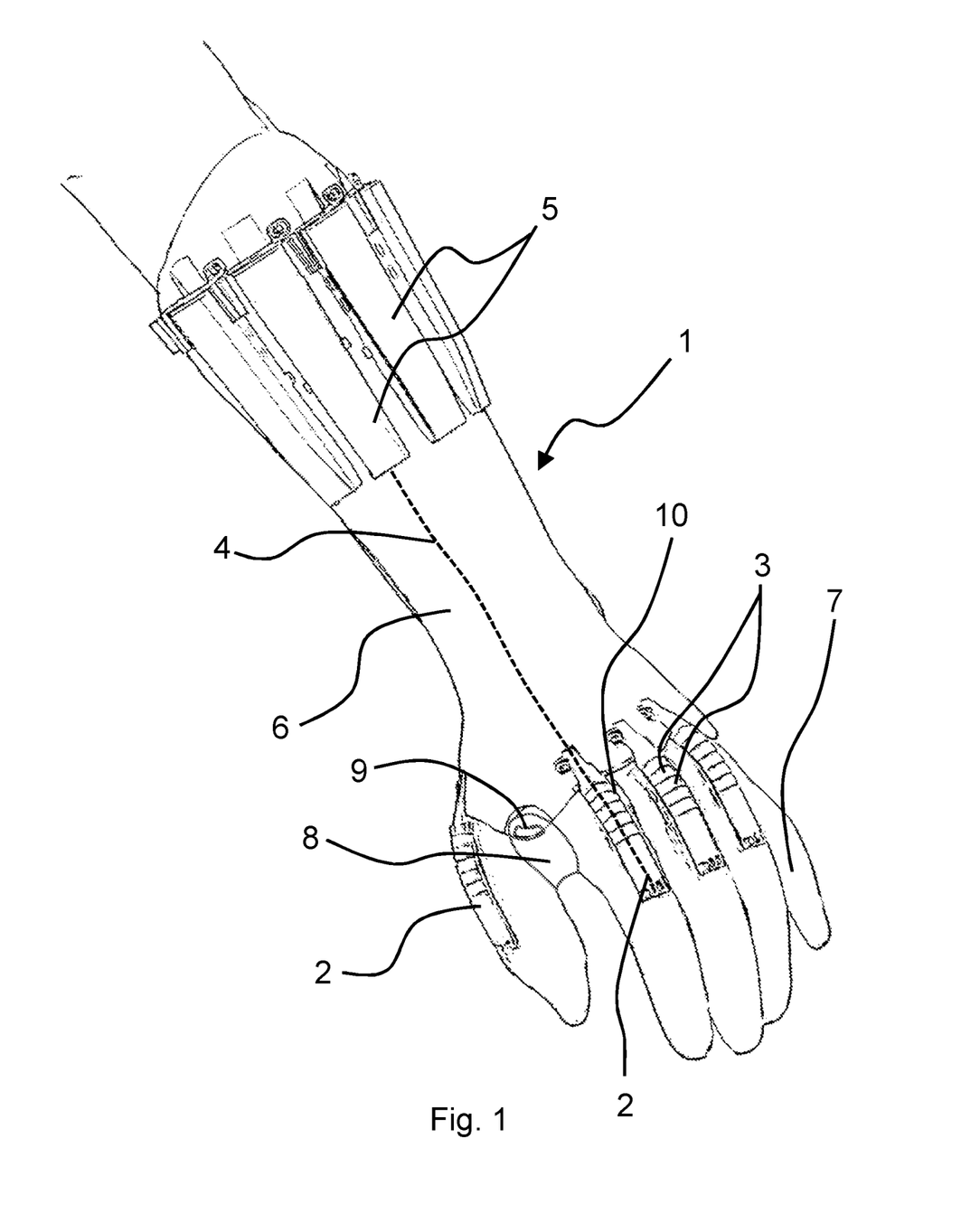
FIG. 1 shows a perspective view of a hand orthosis.

FIG. 1 shows a perspective view of a hand orthosis 1 for bending and/or stretching at least one finger of a patient's hand. The hand orthosis 1 comprises a finger section, in this case a glove section 7 for receiving a patient's hand and a rail 6 for at least partially grasping a patient's forearm, as well as a plurality of force-introducer 5 secured to the rail 6. The force-introducer 5 are each coupled to a finger segment 2 which corresponds to one of the fingers of the patient's hand. The finger segment 2 has a starting segment 38 (FIGS. 4a-4d) connected to the rail 6 and an end segment 39 (FIGS. 7a-7d) connected to the force-introducer 5. Between the starting segment 38 and the end segment 39, at least one articulated segment 40 (FIGS. 5a-5d) for a tilting connection with one of the adjacent segments 38, 39, 40, 41 and at least one linear segment 41 (FIGS. 6a-6d) with limited axial movability on both sides are arranged. The linear segments 41 and the articulated segments 40 are collectively identified as module segments 3 in FIG. 1. The finger segments 2 are each connected at their distal ends by means of coupling elements 4 in the form of wires to a force-introducer 5 in the form of a servomotor, which is attached to the rail 6 that can be secured to the patient's forearm. The coupling elements 4, of which only one is illustrated in dashed form in FIG. 1, are guided and arranged in a concealed manner both in the rail 6 and in the finger segments 2, preferably in a multi-lumen, in particular double-lumen tube.

FIG. 1 shows that the finger section, in this case the glove section 7, is assigned to the distal end of the rail 6 and that the finger segments 2 are secured to the glove section 7. If a tensile or a compressive force is now exerted on the finger segment 2 by the force-introducer 5 via the coupling elements 4, in the case of a tensile force this ensures a stretching, in the case of a compressive force, a bending of the finger segments 2 and thus ultimately also of the fingers connected thereto. To support the palm of the hand, a palm support 8 is connected to the rail 6, preferably in one piece, which grasps the glove section 7 on its side facing the palm and which secures the glove section 7 to the distal end of the rail 6 by means of an additional, detachable latching connection 9. Alternatively, or additionally, the second end of the palmar support 8 can also be firmly, i.e., integrally, connected to the rail 6, so that the rail 6 with the palm support 8 provide an opening for the passage of the thumb of the patient's hand.

In the hand prosthesis 1 shown in FIG. 1, the individual segments 38, 39, 40, 41 of the finger segment 2 are connected to each other by a bayonet connection 10.

Figure 2:
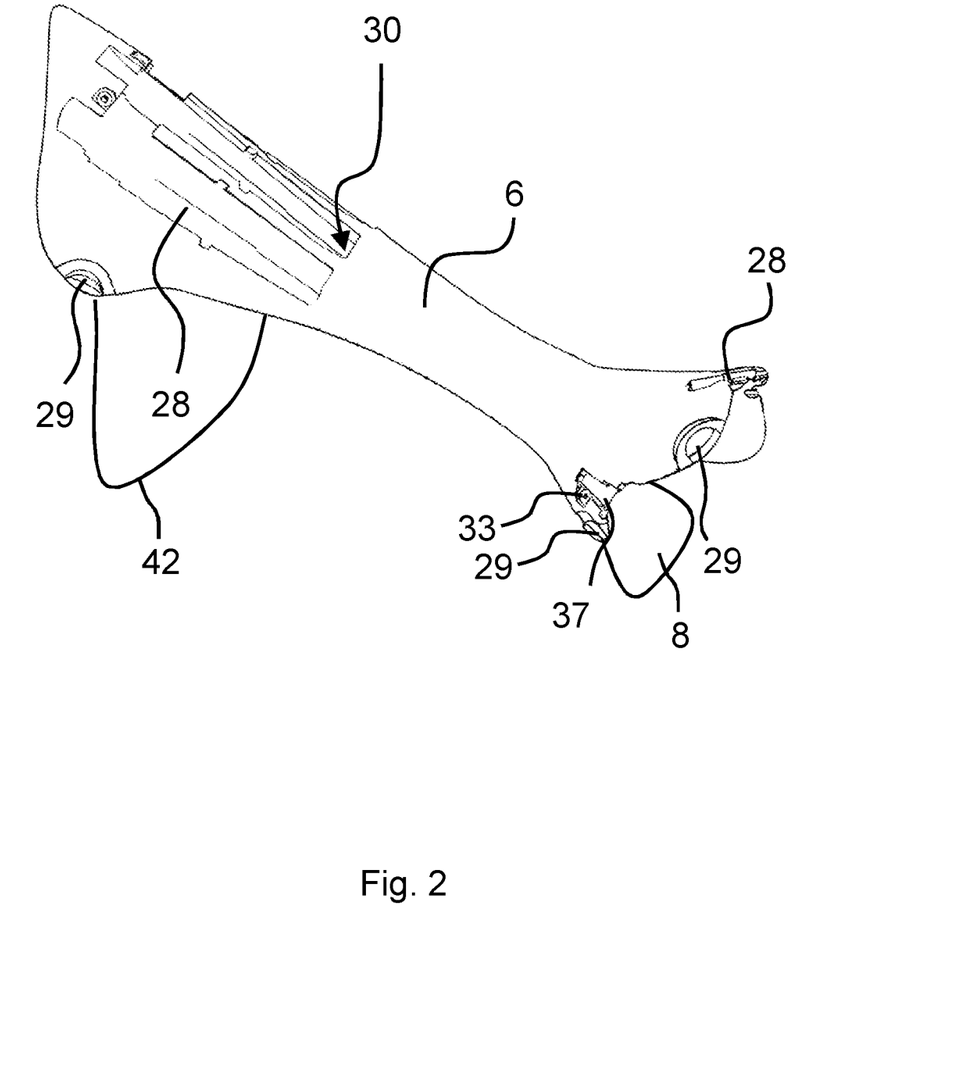
FIG. 2 shows a perspective view of the rail with a palm support and a forearm.

FIG. 2 shows the rail 6 in a perspective side view. This clearly shows in particular that recesses 28 are formed in the rail 6 to accommodate the force-introducer 5 and the starting segments 38 of the finger segments 2. In order to secure the force-introducer 5 and the starting segments 38 in the recesses 28, threaded bushings 33 are incorporated in the rail 6, into which screws can be screwed to fix the force-introducer 5 and the starting segments 38. Optionally, latch-in seats 29 of the latching connection 9 may also be seen, to which a free end of the palm support 8 can be secured. Alternatively, the palm support 8 may also be formed in one piece with the rail 6. Furthermore, it can be seen from FIG. 2 that the rail 6 additionally has a forearm support 42 formed integrally with the rail 6 for at least partially grasping around the patient's forearm. A free end of the forearm support 42 in this case acts like a spring or represents such a spring, which makes it easier for the patient to put on and/or take off the hand orthosis 1 or the rail 6. As an alternative to the forearm support 42, the rail 6 could also have a further latch-in seat 29 into which a securing means—for example a strap with a latching member or a latching recess—can be latched in order to fix the rail 6 to the patient's arm. In addition, the concealed channels 30 run in the rail 6, in which the coupling elements 4, preferably guided in a multi-lumen, in particular double-lumen tube, are accommodated, which transmit the tensile and compressive forces from the force-introducer 5 to the finger segments 2.

Figure 3:
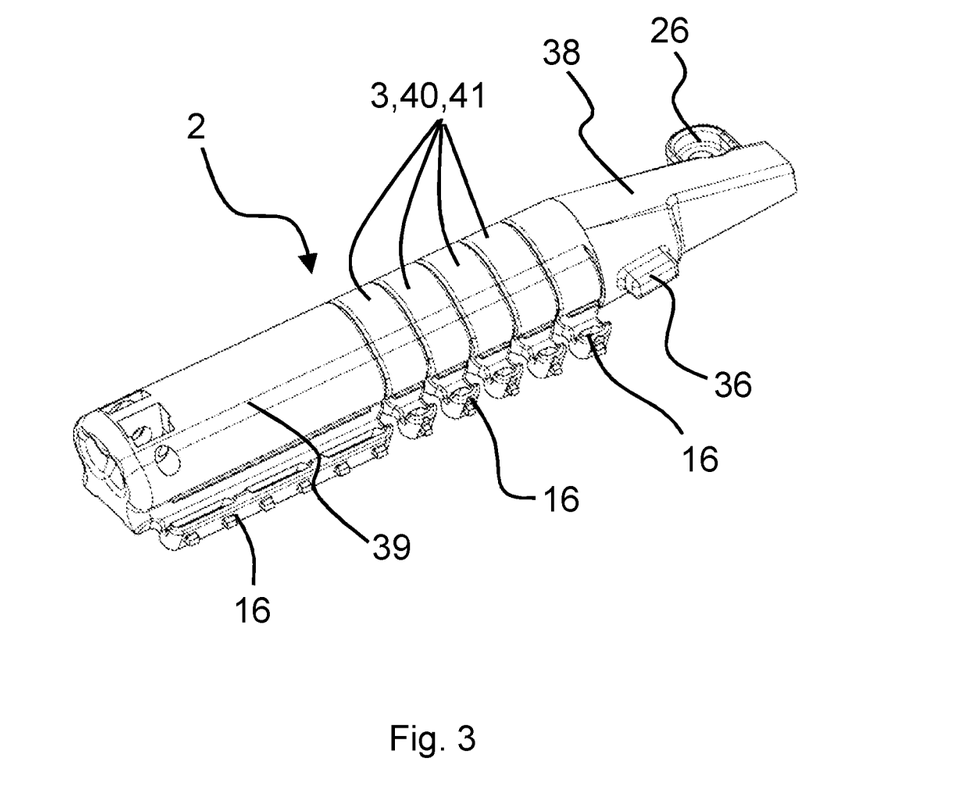
FIG. 3 shows a perspective view of a finger segment.

FIG. 3 shows a perspective view of one of the finger segments 2 of the hand orthosis 1 according to the invention. It can again be seen from FIG. 3 that, in addition to the module segments 3, the finger segment 2 also comprises the distal end segment 39 and a proximal starting segment 38, wherein the starting segment 38 is attached to the rail 6 and the end segment 39 is attached to the glove section 7. To this end, wings 16 are formed on the end segment 39 to be incorporated into the glove section 7. The starting segment 38, on the other hand, additionally has, in addition to the wings 16, a screw receptacle 26 with which the finger segment 2 can be screwed to the rail 6. Moreover, the proximal starting segment 38 may also be assigned insertion aids 36 that can be inserted into corresponding mounting receptacles 37 of the rail 9, whereby the finger segments 2 can be additionally secured to the rail 6 (FIG. 1). One or more of the module segments 3 are arranged between the starting segment 38 and the end segment 39. The module segments 3 are formed either as one of the articulated segments 40 or as one of the linear segments 41.

The articulated segments 40 enable an articulated connection, i.e., a tilting connection which can be pivoted about a pivot axis, and which enables bending at an angle, whereas the linear segments 41 enable translational but non-pivoting adjustment of the segments 38, 39, 40, 41 relative to one another. Consequently, in order to be able to adapt the length of the finger segments 2 to the length of the patient's fingers, and to produce the desired movability of the fingers, it is possible and necessary to vary the number of articulated segments 40 and the number of linear segments 41.

The various segments 38, 39, 40, 41 are or can be coupled to one another, i.e., to the respective adjacent segment 38, 39, 40, 41, via a bayonet connection 10. The operating principle of the respective bayonet connection 10 is explained below with reference to FIGS. 4 to 7.

FIGS. 4a to 4d show several views of the starting segment 38. As explained above, the starting segment 38 has the insertion aid 36 on the side for securing to the rail 6 and two wings 16 each on the side for incorporating the starting segment 38 in the silicone of the glove section 7. The wings 16 of each of the segments 38, 39, 40, 41 have at least one opening 17 and are embodied as a hook shape to form a barb 18, thereby better anchoring the segments 38, 39, 40, 41 in the glove section 7 formed of silicone. In order to be able to wipe off and remove excess silicone material when incorporating the segments 38, 39, 40, 41 in the glove section 7, wiping aids 34 are also provided. When incorporating, excess silicone material can thus be simply wiped off—for example by means of a spatula placed on the wiping aids 34.

Figure 4A:
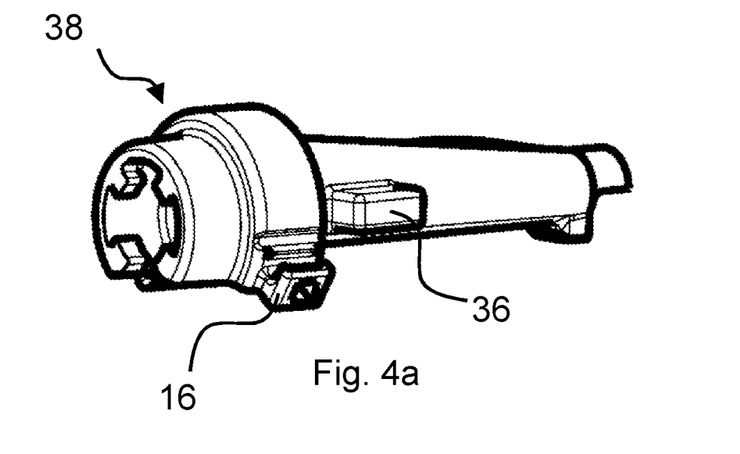
FIG. 4a shows perspective view of a starting segment.
Figure 4B:
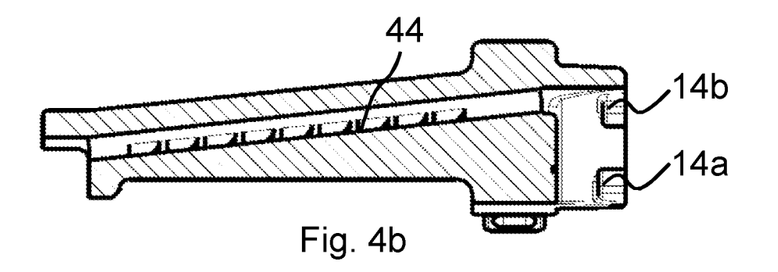
FIG. 4b shows a sectional view of FIG. 4c.
Figure 4C:
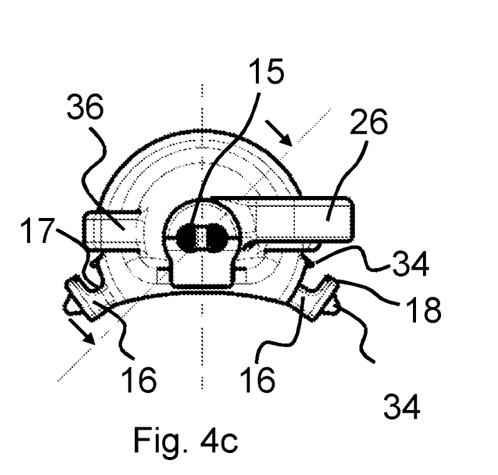
FIG. 4c shows a view of the starting segment facing the rail.
Figure 4D:
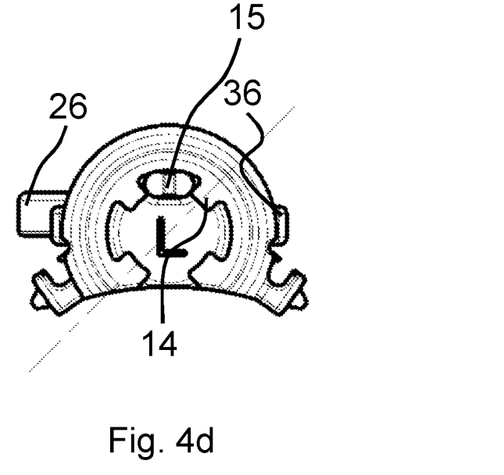
FIG. 4d shows a view of the starting segment facing away from the rail.

Based on the rail-facing view of the starting segment 38 in FIG. 4c, it can also be seen that the starting segment 38 has a lead-through 15 for the coupling elements 4. Preferably, a multi-lumen, in particular double-lumen tube is arranged in or guided through the lead-through 15, in each of which a coupling element 4 formed as a wire—preferably a nitinol wire—is accommodated. FIG. 4d shows a view of the starting segment 38 facing away from the rail, which can be coupled to one of the further module segments 3—either an articulated segment 40 or a linear segment 41—by means of the bayonet connection 10. For this purpose, the starting segment 38 has at least one bayonet hook 14, but preferably four bayonet hooks 14, on an end face 35 facing away from the rail 6, which bayonet hooks 14 can engage in at least one, and preferably in four, bayonet slots 14 of an adjacent module segment 3.

Figure 5A:
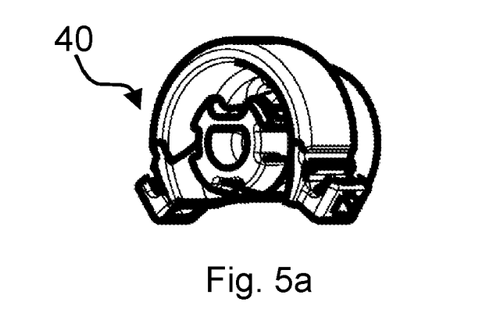
FIG. 5a shows a perspective view of an articulated segment.
Figure 5B:
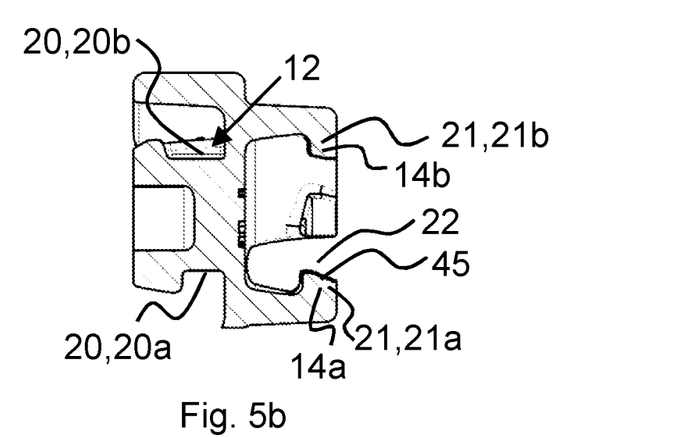
FIG. 5b shows a sectional view of FIG. 5c.
Figure 5C:
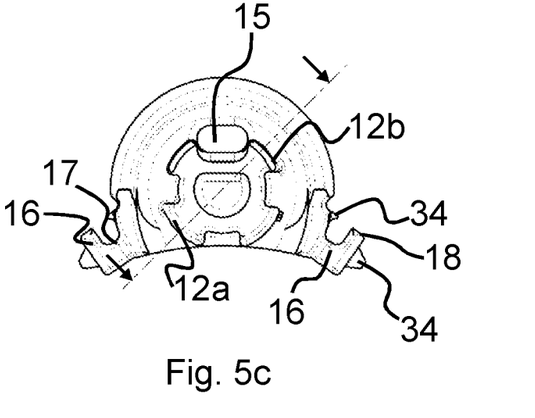
FIG. 5c shows a front view of the articulated segment.
Figure 5D:
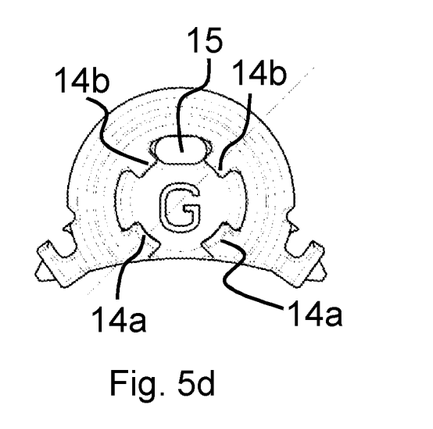
FIG. 5d shows a rear view of the articulated segment.
Figure 6A:
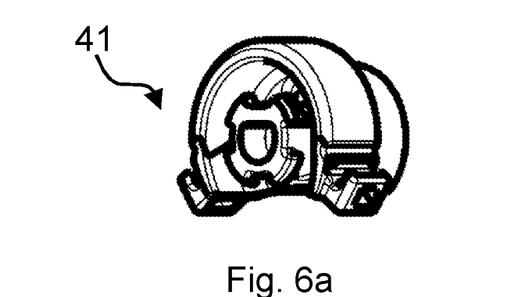
FIG. 6a shows a perspective view of the linear segment.
Figure 6B:
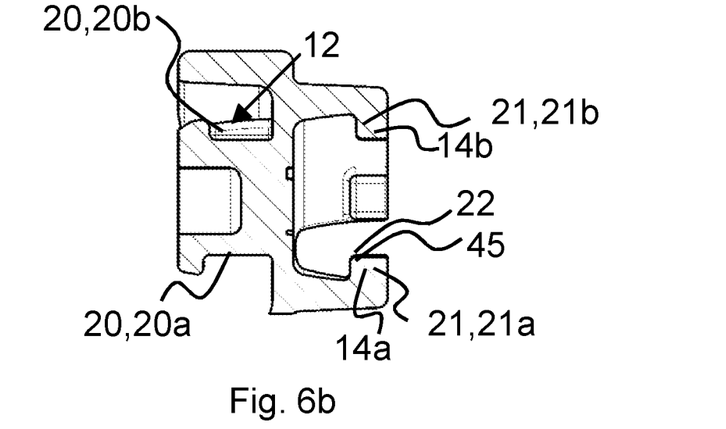
FIG. 6b shows a sectional view of FIG. 6c.
Figure 6C:
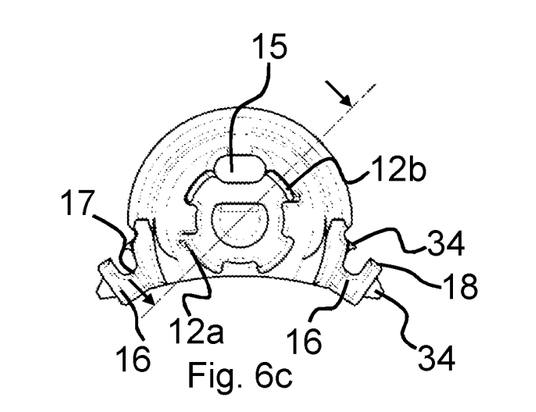
FIG. 6c shows a front view of the linear segment.
Figure 6D:
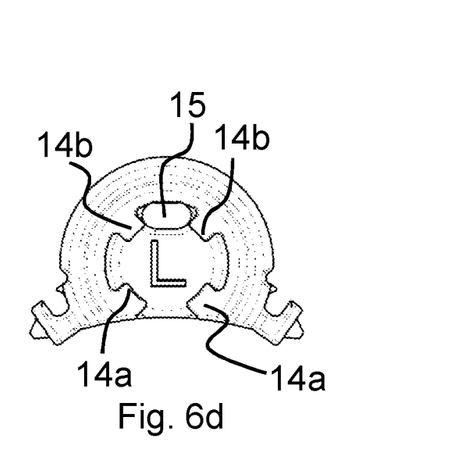
FIG. 6d shows a rear view of the linear segment.
Figure 7A:
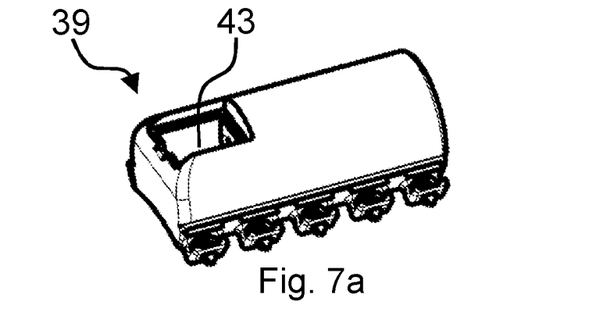
FIG. 7a shows a perspective view of the end segment.
Figure 7B:
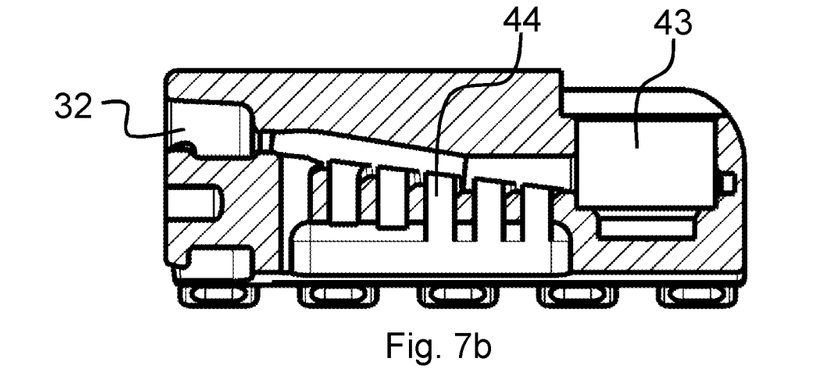
FIG. 7b shows a sectional view of FIG. 7d.
Figure 7C:
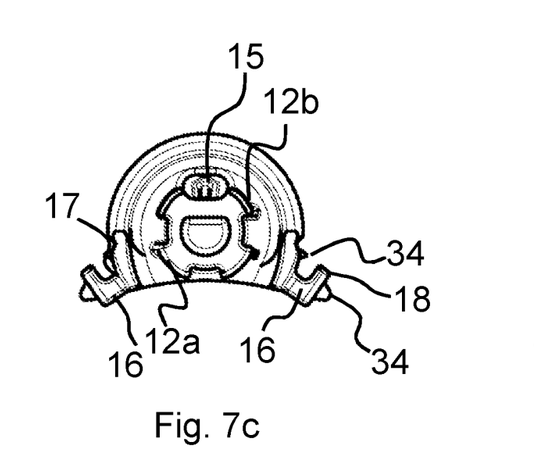
FIG. 7c shows a side of the end segment facing the adjacent segment.
Figure 7D:
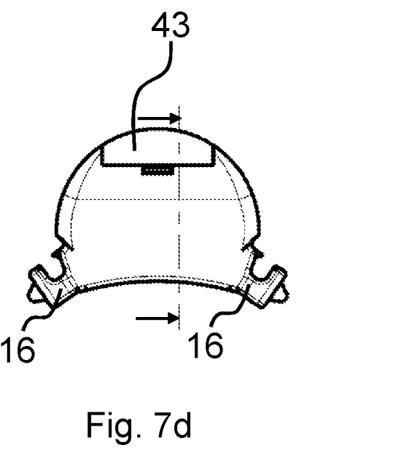
FIG. 7d shows an illustration viewing the free end of the end segment.

FIGS. 5a to 5d show several views of the articulated segment 40. Analogous to the starting segment 38, the articulated segment 40 also has a wing 16 on each side. FIGS. 5b to 5d also illustrate that a number of bayonet slots 12 corresponding to the number of bayonet hooks 14 are formed on one of the end faces. The bayonet hooks 14 serve to engage in the bayonet slots 12 of an adjacent segment 38, 39, 40, 41.

On that end face on which the bayonet hooks 14 are formed, there are a number of projections 21 adapted to the number of bayonet hooks 14, which are engaged behind by the bayonet slots 12 of an adjacent segment 38,39,40 in the assembled state.

Whereas on that end face on which the bayonet slots 12 are formed, there are a total of four receptacles 20 which also engage behind the projections 21 of the adjacent segment 39,40,41 in the assembled state.

In the case of the articulated segment 40, the projections 21 present next to the bayonet slots 12, but at least the two lower projections 21a, are formed with a projection surface 45 running in an inclined manner with respect to the longitudinal axis of the articulated segment 40. The projection surfaces 45 of the projections 21 thereby run towards each other from the outside towards the inside. These inclined projection surfaces 45 enable the tilting movement.

In this case, the depth, i.e., the axial extension along the longitudinal axis, of the projections 21 (in particular of the two lower projections 21a) is equal or approximately equal to the depth, i.e., the axial extension along the longitudinal axis, of the receptacles 20a (in particular of the two lower receptacles 20a). Similarly, the depth of the (lower) bayonet hooks 14, 14a is approximately equal to the depth of the (lower) bayonet slots 12, 12a.

When an articulated segment 40 is connected to an adjacent segment 38, 39, 40, 41, the bayonet hooks 14 of the adjacent segment 38, 39, 40, 41 are inserted through an insertion opening 22 into the bayonet slot 12 of the articulated segment 40 and twisted against each other. Due to the angled design of the lower projections 21a of the articulated segment 40 and due to the fact that the lower bayonet hooks 14a as well as the lower projections 21a have hardly any play in the lower receptacle 20a and in the lower bayonet slot 12a, a translatory movement is prevented, although a tilting movement remains possible due to the inclined projection surfaces 45 of the articulated segments 40.

With reference to FIGS. 6a to 6d, the following is to be noted: In the case of the linear segment 41, the projections 21 present next to the bayonet slots 12, but at least the two lower projections 21a, are formed with a projection surface 45 running parallel or coaxially with respect to the longitudinal axis of the linear segment 41. The projection surfaces 45 of the projections 21 thereby all run coaxially with respect to one another, so that the linear segment 41—unlike the articulated segment 40—lacks a projection surface 45 running at an incline. These projection surfaces 45 enable translation.

The (lower) receptacles 20, 20a at the linear segment 42 have a greater depth than the depth of the (lower) projections 21, 21a. If the bayonet hooks 14 of the linear segment 41 engage in the bayonet slots 12 of the adjacent segment 38, 39, 40, 41, the (lower) bayonet hook 14, 14a and the (upper) bayonet hook 14, 14b have approximately the same amount of play. This allows for translational adjustment. In other words, the depth of the (lower) receptacles 20, 20a of the linear segments 41 and that of the (upper) receptacles 20, 20b are approximately the same. In addition, the depth of the projections 21 of the segments 38, 39, 40, 41 is smaller than the depth of the receptacles 20 of the linear segments 41. In contrast, the depth of the lower receptacles 20, 20a of the articulated segment 40 is smaller than the upper receptacles 20, 20b of the articulated segment 40 and the depth of the lower receptacle 20a is approximately equal to the depth of the lower projections 21a.

FIGS. 7a to 7d show several views of the end segment 39. In contrast to the other segments, a plurality of wings 16, in this case five wings 16 each, are formed laterally on the end segment 39. In particular, it can be seen from FIG. 7c that a bayonet slot 12 is formed on the end segment 39. In addition, it is clear from FIG. 7b that the coupling elements 4 can be secured for coupling with the force-introducer 5 by means of a screw connection 32. In all segments 38, 39, 40, 41, the lead-through 15 is arranged offset upwards relative to the bayonet connection 10, in particular relative to the bayonet hooks 14, in order to ensure better force transmission. The end segment 39 also has a maintenance opening 43 that can be closed with a cover, in order to simplify maintenance of the coupling elements 4. In addition, cavities 44 are formed in the end segment 38 for receiving silicone to improve the incorporation of the end segment 39 in the glove section 7.

Figure 8:
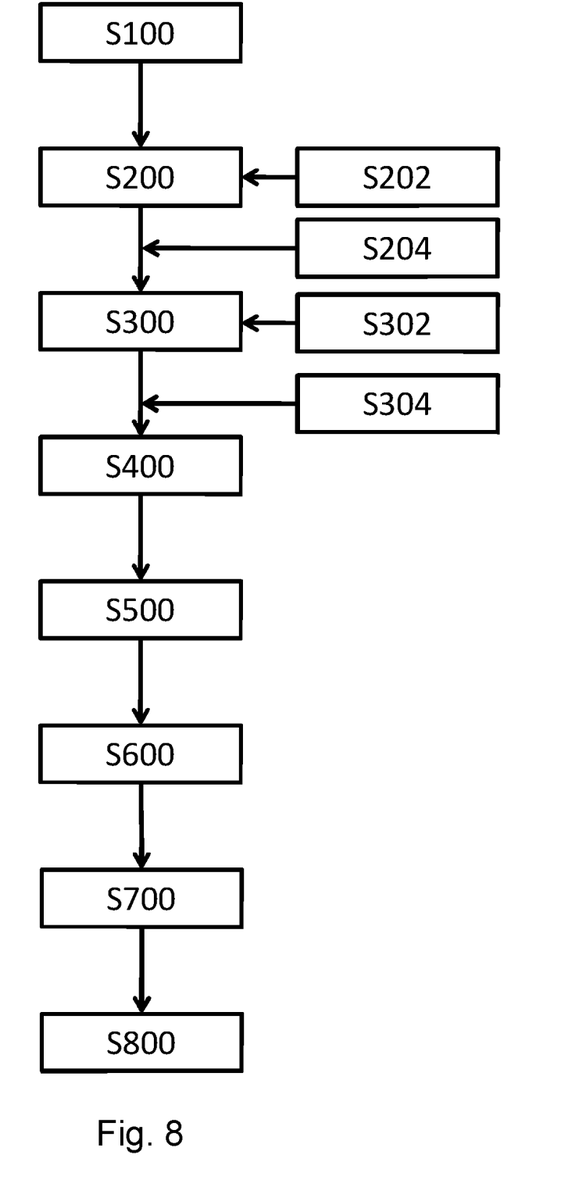
FIG. 8 shows a schematic representation of the method for producing a hand orthosis.

In FIG. 8, the method for producing a hand orthosis 1 is shown in more detail below. First, an impression of at least one finger of a patient's hand, but preferably of all fingers or of the entire patient's hand, and of a forearm is produced (step: S100). Preferably, a plaster cast is produced for this purpose, wherein the plaster cast is presently formed in at least two parts by an upper shell and a lower shell. It can therefore be in several parts. The impression of the fingers and/or the patient's hand can be produced separately from the impression of the forearm. However, it is also possible to create a monolithic impression of the patient's hand and forearm. The impression is preferably made of the patient's hand in a flexed position. The wrist preferably has an extension of 10 degrees to 30 degrees, the MCP joints are stretched, the PIP and DIP joints are flexed by approximately 20 degrees to 50 degrees, and the thumb is in an opposition position or in a lateral position.

The fingers are spread, i.e., there is a gap or distance of at least 5 millimeters (mm) between the index, middle and ring fingers at the level of the PIP. The ring finger and the little finger can be closer than 5 mm. In order to be able to hold this flexed position of the patient's hand more comfortably and securely, it is provided that the flexed position of the patient's hand is held by means of a positioning device. The positioning device can be formed as a block, a wedge or several wedges or blocks which can be combined with each other. In a particularly simple embodiment, the hand is placed around or on a ball.

In the present case, the impression, which is in the form of a negative, is first used to create a reproduction of the at least one finger, preferably of the patient's hand, thus providing a physical model for the further process steps. Subsequently, the finger section, or also the glove section 7, is created on the basis of the reproduction of the at least one finger (S200) by applying several layers of silicone to the reproduction (S202). Silicone with different degrees of hardness is used to create the finger section or the glove section 7. In particular, a first silicone is used in the region of the incorporation of the at least one finger segment 2 and a second silicone is used in the region of a PIP joint and/or a DIP joint of the finger segment 2, wherein the first silicone has a softer degree of hardness than the second silicone. For example, the first silicone has a hardness between 25 and 45 Shore A, preferably 35 Shore A. The second silicone has, for example, a hardness of between 55 and 75 Shore A, preferably 65 Shore A. This makes it possible to make the finger section or glove section 7 stiffer in areas subject to higher stress and softer in areas where flexion or extension occurs. To create a hand orthosis 1 that is individually adapted to the patient, the length of the finger segments 2 is adapted to the length of the patient's fingers (S204). This is done by arranging and coupling one or more module segments 3 between the starting segment 38 coupled to the rail 6 and the end segment 39 coupled to the force-introducer 5. The individual segments 38, 39, 40, 41 are thereby coupled to each other via the above-mentioned bayonet connections 10. In particular, the length and the movability are also adapted by the module segment 3 being formed as a linear segment 41 or as an articulated segment 40, and by the length of the at least one finger segment 2 being adapted by a combination of one or more articulated segments 40 with one or more linear segments 41. The number of linear segments 41 and articulated segments 40 thus determines the length and the movability of the individual phalanges of the finger segment 2.

The at least one finger segment 2 is then incorporated (S300) in the side of the finger section or glove section 7 corresponding to the surface of the hand. This is preferably done by anchoring the finger segments 2 with the wings 16 in the silicone material, i.e., these are surrounded by the silicone, with the silicone penetrating the openings 17 in the process. The barbs 18 provide additional stability. For this purpose, silicone is preferably applied to the underside of the wings 16 and pressed into the cavities 44 and openings 17 using a silicone punch. The finger segments 2 are then pressed onto the finger section or glove section 7 and additionally filled again with silicone from the upper side. Excess silicone protruding over the wiping aids 34 can be removed by means of a spatula. Silicones with different degrees of hardness can also be used here.

At the same time, temporally before or also afterwards, the PIP joint and/or one of the DIP joints is stabilized and/or stiffened by additional incorporating of material into the silicone, wherein the material has a higher degree of hardness than the silicone used (S302).

The silicone of the finger section or glove section 7 is then crosslinked by the action of heat, preferably in an oven.

Padding can now optionally be applied to the reproduction and to the finger section or glove section 7 (S304). In a further step, the physiology of the patient's forearm is now detected using a 3D scan of the reproduction of the forearm based on the impression together with the finger section or glove section 7 and any padding applied, thereby creating a digital 3D model (S400). Alternatively, if no padding is yet applied to the finger section or glove section 7, the physiology of the forearm can also be detected using the impression-based reproduction of the forearm together with the finger section or glove section 7 alone, i.e., without any padding, and a corresponding digital 3D model can be created. An offset can then be added to the digital 3D model created in this way, which is intended for the subsequent application of padding. The offset can correspond to the thickness of the planned padding or be smaller than the planned padding in order to later fit the hand orthosis 1 more closely to the patient's hand.

If the padding has not yet been applied to the finger section or glove section 7, this can also be done after the 3D model has been created and before or after a rail 6 has been created on the basis of the created digital 3D model. Preferably, the entire surface of the finger section or glove section 7 and the rail 6 that come into contact with the patient's hand or forearm is provided with padding. In this case, the rail 6 can be generated on the basis of the 3D model preferably by means of a generative production process (S500), in particular by means of a 3D printing process. During this production, the recesses 28 and the channels 30 required for securing the finger segments 2 and the force-introducer 5 are already machined in. The threaded bushings 33 are then subsequently machined into the rail 6.

Optionally, at least one palm support 8 and/or at least one forearm support 42 can also be added to the digital 3D model, so that the rail 6 generated by means of a generative production process also comprises a palm support 8 and/or a forearm support 42.

In a further step, the force-introducer 5 is secured to the rail 6 in one of the recesses 28 (S600). Simultaneously, previously, or subsequently, the starting segment 38 of the at least one finger segment 2 is secured to a distal end in the recesses 28 of the rail 6 provided for this purpose (S700). For this purpose, the insertion aids 36 formed on the starting segments 38 are inserted into the mounting receptacles 37 of the rail 6 and screwed tightly to the rail 6 with the screw receptacle 26. This is done for all finger segments 2. Finally, the force-introducer 5 are coupled to the finger segments 2 preferably in the area of the distal end, i.e., to the end segments 39 (S800). It should be additionally noted at this point that steps S600, S700 and S800 can be carried out in any order or also simultaneously in accordance with the invention.

In order to provide a smooth surface of the hand orthosis 1, in a final method step, a cover is applied in the form of a covering hood or in the form of a cover to the surface of the rail 6 facing away from the forearm. In particular, the cover covers the area of the recesses 28. The cover is screwed to the rail 6 and concealed and then protects the mostly sensitive force-introducer 5 or servomotors.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for producing a hand orthosis comprising a finger section for receiving a patient's hand, a rail for at least partially grasping a patient's forearm, and at least one finger segment coupled to a force-introducer for flexing and/or stretching at least one finger of a patient's hand, the method comprising:
    producing an impression of at least one finger of a patient's hand and of at least one part of a patient's forearm;

producing at least one finger section using the impression or using a reproduction based on the impression of the at least one finger of the patient's hand;

incorporating at least one finger segment into the side of the finger section corresponding to the hand surface;

detecting the physiology of the patient's forearm using at least one captured image of the impression or of a reproduction of the forearm based on the impression together with the finger section and generating a digital 3D model on the basis of the at least one captured image;

generating a rail based on the generated digital 3D model;

securing at least one force-introducer onto or into the rail;

securing a proximal end of the at least one finger segment to a distal end of the rail; and coupling the at least one force-introducer to the at least one finger segment.

2. The method according to claim 1, wherein the finger section is produced by applying silicone to the impression or to the reproduction based on the impression.

3. The method according to claim 2, wherein the at least one finger segment is incorporated in the silicone using a silicone punch.

4. The method according to claim 3, wherein the module segment is formed as a linear segment or as an articulated segment, and wherein the length of the at least one finger segment is adjusted by combining several module segments or by combining one or more articulated segments with one or more linear segments.

5. The method according to claim 2, wherein different silicones with different degrees of hardness are used to produce the finger section and in that, or silicone with a softer degree of hardness is used in a region of the incorporating of the at least one finger segment, and wherein silicone with a harder degree of hardness is used in a region of a proximal interphalangeal joint (PIP joint) and/or a distal interphalangeal joint (PIP joint) of the finger segment.

6. The method according to claim 2, further comprising: stabilizing and/or stiffening a proximal interphalangeal joint (PIP joint) and/or a distal interphalangeal joint (PIP joint) by additionally incorporating a material in the silicone which has a higher degree of hardness than the silicone.

7. The method according to claim 1, wherein the impression is produced with a bent position of the patient's hand.

8. The method according to claim 7, wherein the bent position is held by a positioning device.

9. The method according to claim 1, further comprising: adapting a length of the at least one finger segment to a length of a patient's finger by arranging and coupling one or more module segments between a starting segment coupled to the rail and an end segment coupled to the force-introducer.

10. The method according to claim 1, wherein the physiology of the forearm and thereby the digital 3D model is detected using the at least one captured image of the impression or the reproduction of the forearm based on the impression, together with the finger section and with padding applied to at least parts of the finger section and/or at least parts of the impression or the at least one reproduction based on the at least one impression.

11. The method according to claim 1, wherein an offset for the application of padding is added to the digital 3D model.

12. The method according to claim 1, further comprising: applying padding to at least a part of a dorsum of the finger section and/or to at least part of the rail.

13. The method according to claim 1, wherein a palm support and/or a forearm support is added to the digital 3D model.

14. The method according to claim 1, wherein, before the physiology of the forearm is detected using the at least one captured image, at least one marking line or a plurality of marking points are applied to the impression or to the reproduction based on the impression for defining a subsequent contour of the rail.

* * * * *